United States Patent [19]
Brown

[11] Patent Number: 5,770,611
[45] Date of Patent: Jun. 23, 1998

[54] INDOLE DERIVATIVES AS $5HT_1$-LIKE AGONISTS

[75] Inventor: Alan Daniel Brown, Sandwich, United Kingdom

[73] Assignee: Pfizer Inc., New York, N.Y.

[21] Appl. No.: 809,600

[22] PCT Filed: Sep. 29, 1995

[86] PCT No.: PCT/EP95/03884

§ 371 Date: Apr. 3, 1997

§ 102(e) Date: Apr. 3, 1997

[87] PCT Pub. No.: WO96/11195

PCT Pub. Date: Apr. 18, 1996

[30] Foreign Application Priority Data

Oct. 11, 1994 [GB] United Kingdom ............ 9420503

[51] Int. Cl.$^6$ ............ C07D 403/14; C07D 405/14; A61K 31/40; A61K 31/445
[52] U.S. Cl. ............ 514/323; 514/414; 546/201; 548/468
[58] Field of Search ............ 546/201; 548/468; 514/323, 414

[56] References Cited

U.S. PATENT DOCUMENTS

| | | | |
|---|---|---|---|
| 5,409,941 | 4/1995 | Nowakowski | 514/339 |
| 5,498,626 | 3/1996 | Macor | 514/414 |
| 5,545,644 | 8/1996 | Macor et al. | 514/323 |
| 5,559,129 | 9/1996 | Macor et al. | 514/323 |
| 5,559,246 | 9/1996 | Macor et al. | 548/468 |
| 5,578,612 | 11/1996 | Macor et al. | 514/323 |
| 5,594,014 | 1/1997 | Macor et al. | 514/364 |
| 5,607,951 | 3/1997 | Macor et al. | 514/414 |
| 5,607,960 | 3/1997 | Wythes | 514/414 |
| 5,618,834 | 4/1997 | Butler | 514/415 |
| 5,639,752 | 6/1997 | Macor | 514/245 |

FOREIGN PATENT DOCUMENTS

| | | |
|---|---|---|
| 9321177 | 10/1993 | WIPO. |
| 9321178 | 10/1993 | WIPO. |
| 9424127 | 10/1994 | WIPO. |

*Primary Examiner*—Mukund J. Shah
*Assistant Examiner*—Deepak R. Rao
*Attorney, Agent, or Firm*—Peter C. Richardson; Paul H. Ginsburg; Grover F. Fuller, Jr.

[57] ABSTRACT

Compounds of formula (I), pharmaceutically acceptable salts thereof, and pharmaceutically acceptable solvates (including hydrates) of either entity, wherein $R^1$ is (a) $R^2$ is $R^3R^4C(OH)A$; V is C=O or $CH_2$; W is O or $NR^5$; $R^3$ and $R^4$ are each independently selected from H and $C_1$–$C_4$ alkyl; or, together with the carbon atom to which they are attached, form a 4- or 5-membered carbocyclic ring; $R^5$ is H, benzyl, $C_1$–$C_5$ alkanoyl or $SO_2(C_1$–$C_4)$alkyl; A is $C_2$–$C_3$ alkylene; m is 0 or 1; and n is 0 or 1; with the provisos that when n is 1 and V is C=O then W is NH, and when n is 1 and V is $CH_2$ then W is O; are selective $5$-$HT_1$-like agonists useful in the treatment of, inter alia, migraine, cluster headache, chronic paroxysmal hemicrania and headache associated with vascular disorders.

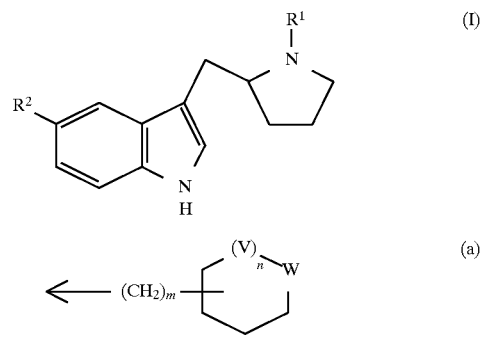

9 Claims, No Drawings

INDOLE DERIVATIVES AS 5HT$_1$-LIKE AGONISTS

This is the national stage under 35 U.S.C. 371 of application no. PCT/EP95/03884 filed Sep. 29, 1995.

The present invention relates to indole derivatives which act on 5-hydroxytryptamine (5-HT) receptors.

More particularly the present invention relates to 3,5-disubstituted indoles which are selective agonists at the "5-HT$_1$-like" subtype of the 5-hydroxytryptamine receptor. Such "5-HT$_1$-like" receptors are present in the carotid vascular bed and their activation causes vasoconstriction with a consequent reduction in carotid blood flow. Compounds which have "5-HT-like" agonist activity are therefore useful in the treatment of medical conditions which are thought to result from excessive dilation of the carotid bed, such as migraine, cluster headache, chronic paroxysmal hemicrania and headache associated with vascular disorders. Certain compounds of the present invention are also agonists at central 5-HT$_1$ receptors and are therefore useful for the treatment of depression, anxiety, eating disorders, obesity, drug abuse and emesis.

The present invention provides compounds of formula:

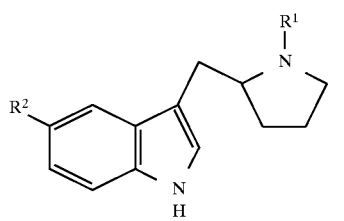

and pharmaceutically acceptable salts thereof, and pharmaceutically acceptable solvates (including hydrates) of either entity, wherein R$^1$ is

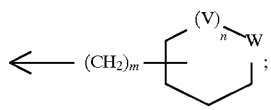

R$^2$ is R$^3$R$^4$C(OH)A;
V is C=O or CH$_2$;
W is O or NR$^5$;
R$^3$ and R$^4$ are each independently selected from H and C$_1$–C$_4$ alkyl; or, together with the carbon atom to which they are attached, form a 4- or 5-membered carbocyclic ring;
R$^5$ is H, benzyl, C$_1$–C$_5$ alkanoyl or SO$_2$(C$_1$–C$_4$)alkyl;
A is C$_2$–C$_3$ alkylene;
m is 0 or 1;
and
n is 0 or 1;
with the provisos that when n is 1 and V is C=O then W is NH, and when n is 1 and V is CH$_2$ then W is O.

In the above definition, unless otherwise indicated, alkyl groups having three or more carbon atoms and alkanoyl groups having four or more carbon atoms may be straight chain or branched chain.

The compounds of formula (I) may contain one or more asymmetric centres and thus can exist as stereoisomers, i.e. as enantiomers or as diastereoisomers, and the invention includes both the separated individual stereoisomers as well as mixtures thereof.

The preferred stereoisomers are those compounds of formula (IA) which possess the R-configuration at the 2-position of the pyrrolidine ring, as represented by formula (IA):

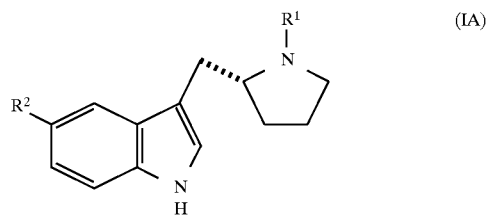

Also included in the invention are radiolabelled derivatives of compounds of formula (I) which are suitable for biological studies.

The pharmaceutically acceptable salts of compounds of formula (I) are, for example, non-toxic acid addition salts formed with inorganic acids such as hydrochloric, hydrobromic, sulphuric and phosphoric acid, with organo-carboxylic acids, or with organo-sulphonic acids. For a review of suitable pharmaceutical salts, see J. Pharm. Sci., 1977, 66, 1–19.

A preferred group of compounds of formula (I) is that wherein W is NR$^5$; R$^3$ and R$^4$ are both methyl; R$^5$ is H, benzyl, COCH$_3$ or SO$_2$CH$_3$; A is ethylene; m is 0 or 1; and n is 0.

A more preferred group of compounds of formula (I) is that wherein W is NR$^5$; R$^3$ and R$^4$ are both methyl; R$^5$ is benzyl or SO$_2$CH$_3$; A is ethylene; m is 1; and n is 0.

Particularly preferred individual compounds of the invention include:

3-[N-(N-benzyl-3(R,S)-pyrrolidinylmethyl)-2(R)-pyrrolidinylmethyl]-5-(3-hydroxy-3-methyl-1-butyl)-1H-indole and 5-(3-hydroxy-3-methyl-1-butyl)-3-[N-(N-methanesulphonyl- 2(R)-pyrrolidinylmethyl)-2(R)-pyrrolidinylmethyl]-1H-indole;

and pharmaceutically acceptable salts thereof, and pharmaceutically acceptable solvates (including hydrates) of either entity.

In another aspect, the present invention provides processes for the preparation of compounds of formula (I), their pharmaceutically acceptable salts, and pharmaceutically acceptable solvates (including hydrates) of either entity, as illustrated below. It will be appreciated by persons skilled in the art that, within the various processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps. It will also be appreciated that various standard transformations within certain compounds of formula (I) will provide other compounds of formula (I); examples are debenzylation of N-benzylpyrrolidine groups, and N-acylation and N-sulphonylation of the N-unsubstituted pyrrolidines thus formed.

A compound of formula (I) may be obtained by selective N-alkylation of the saturated heterocyclic ring of a compound of formula (II):

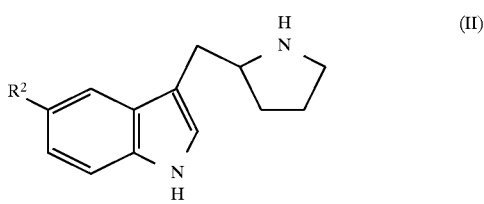

wherein $R^2$ is as previously defined for formula (I), using one or more of the following methods.

1. By reaction of a compound of formula (II) with a compound of formula $R^1X$, wherein $R^1$ is as defined for formula (I) or is a conventionally protected precursor thereof (e.g. containing —NH protected as the benzyl, Boc or Z derivative), and X is a suitable leaving group, e.g. halo (preferably chloro, bromo or iodo), $C_1$–$C_4$ alkanesulphonyloxy, trifluoromethanesulphonyloxy or arylsulphonyloxy (preferably benzenesulphonyloxy or p-toluenesulphonyloxy), in the presence of an appropriate base, e.g. sodium or potassium carbonate or bicarbonate, or triethylamine, in a suitable solvent such as $C_1$–$C_4$ alkanol, 1,2-dimethoxyethane, acetonitrile, dimethylformamide or N,N-dimethylacetamide, and optionally in the presence of sodium or potassium iodide, and/or 4-dimethylaminopyridine. The reaction can be conducted at from about 0° C. to about 150° C., preferably at from about room temperature to about 100° C., and, where appropriate, is followed by a standard deprotection step.

2. By reductive alkylation of a compound of formula (II) using the appropriate aldehyde-, ketone- or carboxylic acid- containing $R^1$ precursor. In the case of an aldehyde or ketone precursor, the substrate (II) and carbonyl reagent may be reacted together under conventional catalytic hydrogenation conditions or in the presence of sodium cyanoborohydride, in a suitable solvent such as methanol or ethanol, at about room temperature. Alternatively, the reductive alkylation may be achieved by a two-step procedure in which the intermediate enamine is formed initially, under conventional conditions, and subsequently reduced to the required amine, e.g. using sodium cyanoborohydride in tetrahydrofuran-methanol at about room temperature.

In the case of a carboxylic acid precursor, the substrate (II) and the said acid reagent may be reacted together in the presence of excess sodium borohydride in a suitable solvent; preferably the carboxylic acid itself is used as solvent whenever possible. Since this reductive alkylation proceeds via in situ formation of the corresponding sodium triacyloxyborohydride, obvious variations are to employ preformed reagent when commercially available or to preform it in a separate in situ step using the stoichiometric amount of carboxylic acid in a suitable solvent. An example of the latter procedure involves the treatment of six equivalents of the carboxylic acid with two equivalents of sodium borohydride in dry tetrahydrofuran at about room temperature. When formation of the required sodium triacyloxyborohydride is complete, the reaction mixture is treated with a solution of one equivalent of the substrate (II) in the same solvent and the subsequent reaction step is conducted at from about room temperature to about 70° C., preferably at about 50°–55° C.

3. When $R^1$ contains an electron withdrawing group such as —CONH— in the β-position with respect to the point of attachment of $R^1$ to the pyrrolidine nitrogen atom, by conjugate addition (Michael-type reaction) of a compound of formula (II) to the corresponding α,β-unsaturated amide-containing $R^1$ precursor, optionally in the presence of a tertiary amine base such as triethylamine. The reaction may optionally be conducted in a suitable solvent, e.g. 1,2-dimethoxyethane or N,N-dimethylacetamide, at from about 0 °C. to about 100° C., preferably at about 85° C. or about 100° C. respectively. Alternatively, the reaction may be effected in pyridine, which serves both as tertiary amine base and as solvent, preferably at about 115° C.

Certain compounds of formula (I) can be prepared from other compounds of formula (I) by, for example, the following standard transformations within the $R^1$ substituent:

(a) a compound of formula (I) wherein $R^5$ is H is obtainable from the corresponding compound of formula (I) wherein $R^5$ is benzyl by conventional debenzylation procedures, e.g. catalytic hydrogenation. Preferably the reaction is effected using palladium as catalyst and conducted in a suitable solvent such as ethanol at about room temperature and atmospheric pressure.

(b) a compound of formula (I) wherein $R^5$ is $C_1$–$C_5$ alkanoyl or $SO_2(C_1$–$C_6$ alkyl) is obtainable from the corresponding compound of formula (I) wherein $R^5$ is H by conventional acylation or sulphonylation procedures, respectively, e.g. by using the appropriate acyl or sulphonyl halide or anhydride in a suitable solvent, optionally in the presence of a base, at from about 0° C. to about 85° C. Preferably the solvent is dichloromethane, the base is a tertiary amine such as triethylamine, and the reaction temperature is from about 0° C. to about 40° C.

A compound of formula (II) may be obtained from a compound of formula (III):

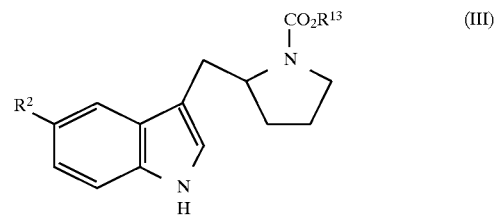

wherein $R^2$ is as previously defined for formula (II) and $R^{13}$ forms part of a conventional amino acid N-protecting group, i.e. a carbamate, wherein $R^{13}$ is preferably benzyl or t-butyl. N-Deprotection of a compound of formula (III) can be achieved using standard methodology; for example, when $R^{13}$ is benzyl, by palladium-catalysed hydrogenolysis and, when $R^{13}$ is t-butyl, by protonolysis using trifluoroacetic acid or hydrogen chloride.

Alternatively, when $R^{13}$ is benzyl, N-deprotection can be effected by modification of the procedure reported in Tetrahedron Letters, 1988, 29, 2983, in which (III) is treated with an excess of a tri(lower alkyl)silane in the presence of a palladium(II) salt and an excess of a tri(lower alkyl)amine in a suitable solvent such as a $C_1$–$C_4$ alkanol. Preferably the reaction is conducted using triethylsilane, palladium(II) acetate and triethylamine in ethanol at about room temperature.

A compound of formula (III) may be obtained from a compound of formula (IV):

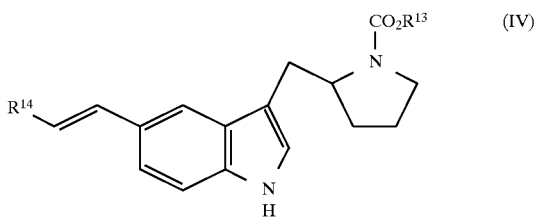

wherein $R^{14}$ is $R^3R^4C(OH)$ or $R^3R^4C(OH)CH_2$, and $R^{13}$ is as previously defined for formula (III). This may be achieved by conventional catalytic or catalytic transfer hydrogenation, preferably using palladium as catalyst and, in the latter process, ammonium formate as the hydrogen source. Alternatively, the trialkylsilane/palladium(II) salt procedure described above may be employed.

Clearly, when $R^{13}$ is benzyl, a compound of formula (IV) may be converted directly to a compound of formula (II) wherein $R^2$ is $CH_2CH_2R^{14}$ under these conditions.

A compound of formula (IV) may be obtained from a compound of formula (V):

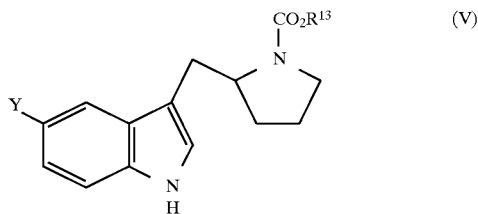

wherein Y is chloro, bromo or iodo (preferably bromo), and $R^{13}$ is as previously defined for formula (IV), with an alkene of formula $CH_2=CHR^{14}$, wherein $R^{14}$ is as previously defined for formula (IV), using the Heck reaction. Thus the desired coupling is achieved using, for example, an excess of the required alkene, in the presence of palladium(II) acetate, tri-o-tolylphosphine and triethylamine, in a suitable solvent such as acetonitrile or dimethylformamide, at from about 80° C. to about 160° C.

A compound of formula (V) may be obtained as described in WO-A-93/21177.

An alternative approach to a compound of formula (I) involves the reaction of a compound of formula (VI):

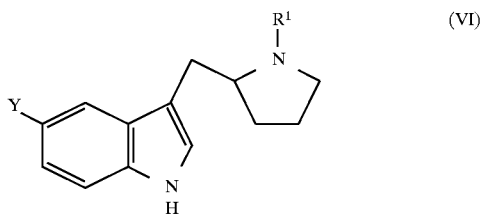

wherein $R^1$ is as previously defined for formula (I) and Y is as previously defined for formula (V), with an alkene of formula $CH_2=CHR^{14}$ wherein $R^{14}$ is as previously defined for formula (IV), under the Heck reaction conditions previously described for the conversion of (V) to (IV), followed by reduction of the resulting alkene as already described for the reduction of (IV) to (III) or directly to (II).

A compound of formula (VI) may be obtained by selective N-alkylation of a compound of formula (VII):

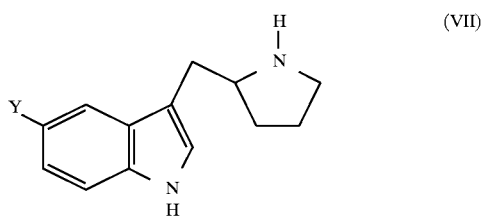

wherein Y is as previously defined for formula (VI), by analogy with the procedures described earlier for the conversion of (II) to (I).

A compound of formula (VII) may be obtained from a compound of formula (V) wherein $R^{13}$ and Y are as previously defined for formula (V) by the standard N-deprotection methodology already described. Preferably however, when $R^{13}$ is benzyl, deprotection is effected by a non-hydrogenolytic procedure such as protonolysis in a suitable solvent using, for example, hydrogen bromide in glacial acetic acid or hydrogen chloride in methanol, at about room temperature, a Lewis acid-catalysed nucleophilic deprotection using, for example, boron trifluoride etherate and excess ethanethiol in a suitable solvent such as dichloromethane at about room temperature, or an alkaline deprotection using, for example, potassium hydroxide in a suitable solvent such as a $C_1$–$C_4$ alkanol, preferably n-butanol.

Compounds of formula $CH_2=CHR^{14}$ wherein $R^{14}$ is as previously defined for formula (IV), and the various reagents required for the processes hereinbefore disclosed, when neither commercially available nor subsequently described, can be obtained either by analogy with the reactions described in the Examples and Preparations sections or by conventional synthetic procedures, in accordance with standard textbooks on organic chemistry or literature precedent, from readily accessible starting materials using appropriate reagents and reaction conditions. Clearly, when the preferred stereoisomers of formula (IA) are required, the compounds of formula (V) will possess the 2R-configuration.

Persons skilled in the art will recognise that the alkenes depicted hereinbefore may be obtained in cis- or trans-stereoisomeric forms, or as mixtures of cis- and trans-stereoisomers, and are represented in one such form only in the interests of clarity and convenience. Such persons will also be aware of variations of, and alternatives to, those reactions described hereinafter for the preparation of compounds of formula (I).

The pharmaceutically acceptable acid addition salts of compounds of formula (I) may also be prepared in a conventional manner. For example a solution of the free base is treated with the appropriate acid, either neat or in an appropriate solvent, and the resulting salt isolated either by filtration or by evaporation under vacuum of the reaction solvent. Certain such salts may be formed or interconverted using ion-exchange resin techniques.

The compounds of the invention are selective agonists at the "5-$HT_1$-like" subtype of the 5-HT (serotonin) receptor and are therefore useful in the curative or prophylactic treatment of migraine and associated conditions such as cluster headache, chronic paroxysmal hemicrania and headache associated with vascular disorders. Certain of these compounds are also agonists at central 5-$HT_1$ receptors and are therefore useful for the treatment of depression, anxiety, eating disorders, obesity, drug abuse and emesis.

The in vitro evaluation of the "5-$HT_1$-like" receptor agonist activity of the compounds of the invention is carried out by testing the extent to which they mimic sumatriptan in contracting the isolated dog saphenous vein strip (P.P.A. Humphrey et al., Brit. J. Pharmacol., 1988, 94, 1123). This effect can be blocked by methiothepin, a known 5-HT antagonist. Sumatriptan is known to be useful in the treatment of migraine and produces a selective increase in carotid vascular resistance in the anaesthetized dog and a consequent decrease in carotid arterial blood flow. It has been suggested (W. Feniuk et al., Brit. J. Pharmacol., 1989, 96, 83) that this is the basis of its efficacy.

The $5\text{-}HT_1$ agonist activity of the compounds of the invention can be measured in in vitro receptor binding assays as described for the $5\text{-}HT_{1A}$ receptor, using rat cortex as the receptor source and $[^3H]8\text{-}OH\text{-}DPAT$ as the radioligand (D. Hoyer et al., Europ. J. Pharmacol., 1985, 118, 13), and as described for the $5\text{-}HT_{1D}$ receptor, using bovine caudate as the receptor source and $[^3H]5\text{-}HT$ as the radioligand (R. E. Heuring and S. J. Peroutka, J. Neuroscience, 1987, 7, 894).

In therapy, the compounds of formula (I), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example, intravenously, intramuscularly or subcutaneously. For parenteral administration, they are best used in the form of a sterile aqueous solution which may contain other substances, for example, enough salts or glucose to make the solution isotonic with blood. For buccal or sublingual administration they may be administered in the form of tablets or lozenges which can be formulated in a conventional manner.

For oral, parenteral, buccal and sublingual administration to patients, the daily dosage level of the compounds of formula (I), their pharmaceutically acceptable salts, and pharmaceutically acceptable solvates of either entity, will be from 0.1 ng to 20 mg/Kg (in single or divided doses). Thus tablets or capsules will contain from 5 ng to 0.5 g of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of formula (I), their pharmaceutically acceptable salts, and pharmaceutically acceptable solvates of either entity, can be administered in the form of a suppository or pessary, or they may be applied topically in the form of a lotion, solution, cream, ointment or dusting powder. For example, they can be incorporated into a cream consisting of an aqueous emulsion or polyethylene glycols or liquid paraffin; or they can be incorporated, at a concentration of from 1 to 10%, into an ointment consisting of a white wax or white soft paraffin base together with such stabilisers and preservatives as may be required.

The compounds of formula (I), their pharmaceutically acceptable salts, and pharmaceutically acceptable solvates of either entity, can also be administered intranasally or by inhalation and are conveniently delivered in the form of a solution or suspension from a pump spray container, which is squeezed or pumped by the patient, or as an aerosol spray presentation from a pressurised container or a nebuliser with the use of a suitable propellant, e.g. dichlorodifluoromethane, trichlorofluoromethane, dichlorotetrafluoroethane, carbon dioxide or other suitable gas. In the case of a pressurised aerosol, the dosage unit may be determined by providing a valve to deliver a metered amount. The pressurised container or nebuliser may contain a solution or suspension of the active compound. Capsules and cartridges (made, for example, from gelatin) for use in an inhaler or insufflator may be formulated containing a powder mix of a compound of the invention and a suitable powder base such as lactose or starch.

Aerosol formulations are preferably arranged so that each metered dose or "puff" of aerosol contains from 1 ng to 1000 µg of a compound of formula (I), or a pharmaceutically acceptable salt thereof, or a pharmaceutically acceptable solvate of either entity, for delivery to the patient. The overall daily dose with an aerosol will be within the range of from 5 ng to 10 mg which may be administered in a single dose or, more usually, in divided doses throughout the day.

Thus the invention provides pharmaceutical compositions comprising a compound of formula (I), or a pharmaceutically acceptable salt thereof, or a pharmaceutically acceptable solvate (including hydrate) of either entity, together with a pharmaceutically acceptable diluent or carrier.

The invention also provides a compound of formula (I), or a pharmaceutically acceptable salt thereof, or a pharmaceutically acceptable solvate (including hydrate) of either entity, or a pharmaceutical composition containing any of the foregoing, for use as a medicament.

The invention further includes the use of a compound of formula (I), or a pharmaceutically acceptable salt thereof, or a pharmaceutically acceptable solvate (including hydrate) of either entity, or a pharmaceutical composition containing any of the foregoing, both for the manufacture of a medicament for the curative or prophylactic treatment of migraine or an associated condition such as cluster headache, chronic paroxysmal hemicrania or headache associated with a vascular disorder, or of depression, anxiety, an eating disorder, obesity, drug abuse or emesis, and also for the manufacture of a medicament for the curative or prophylactic treatment of a medical condition for which a selective agonist of $5\text{-}HT_1$-like receptors is indicated.

In a further aspect, the invention provides both a method of treating a human being to cure or prevent migraine or an associated condition such as cluster headache, chronic paroxysmal hemicrania or headache associated with a vascular disorder, or depression, anxiety, an eating disorder, obesity, drug abuse or emesis, and also a method of treating a human being to cure or prevent a medical condition for which a selective agonist of $5\text{-}HT_1$-like receptors is indicated, which comprises treating said human being with an effective amount of a compound of formula (I), or a pharmaceutically acceptable salt thereof, or a pharmaceutically acceptable solvate (including hydrate) of either entity, or a pharmaceutical composition containing any of the foregoing.

The syntheses of the compounds of the invention and of the intermediates for use therein are illustrated by the following Examples and Preparations. The purity of the compounds was routinely monitored by thin layer chromatography (Rf) using Merck Kieselgel 60 $F_{254}$ plates and the following solvent systems (SS):

1. dichloromethane:methanol:0.880 aqueous ammonia, 90:10:1;
2. hexane:ethyl acetate, 3:1;
3. hexane:ethyl acetate, 1:1.

¹H Nuclear magnetic reasonance (NMR) spectra were recorded using either a Nicolet QE-300 or a Bruker AC-300 spectrometer and were in all cases consistent with the proposed structures.

LRMS means low resolution mass spectrum.

Room temperature means 20°–25° C.

EXAMPLE 1

3-[N-(N-Benzyl-3(R,S)-pyrrolidinylmethyl)-2(R)-pyrrolidinylmethyl]-5-(3-hydroxy-3-methyl-1-butyl-1H-indole A stirred mixture of 5-(3-hydroxy-3-methyl-1-butyl-3(2(R)-pyrroldinylmethyl)-1H-indole (Preparation 3; 400 mg, 1.35 mmol), N-benzyl-3(R,S)-p-toluene-sulphonyloxymethylpyrrolidine (Preparation 7; 465 mg, 1.35 mmol), anhydrous sodium carbonate (130 mg, 1.23 mmol), sodium iodide (203 mg, 1.35 mmol) and 1,2-dimethoxyethane (12 ml), under nitrogen, was heated under reflux for 52 hours. The cool reaction mixture was partitioned between ethyl acetate (100 ml) and 2M aqueous sodium carbonate solution (100 ml), then the organic phase separated, washed with 2M aqueous sodium carbonate solution, dried ($Na_2SO_4$) and filtered. Evaporation of the filtrate under reduced pressure gave the crude product which was purified by column chromatography on silica gel, eluting with dichloromethane:methanol:0.880 aqueous ammonia (90:10:0.2), to afford the title compound (439 mg) as an off-white foam. Rf 0.60 (SS 1). $[\alpha]_D^{25}+16°$ (c=0.1, $CH_3OH$). Found: C,73.85; H,8.63; N,8.45. $C_{30}H_{41}N_3O$; 0.42 $CH_2Cl_2$ requires C,73.79; H,8.52; N,8.49%.

EXAMPLE 2

5-(3-Hydroxy-3-methyl-1-butyl)-3-[N-(3(R,S)-pyrrolidinylmethyl)-2(R)-pyrrolidinylmethyl]-1H-indole A stirred solution of the title compound of Example 1 (530 mg, 1.07 mmol) in ethanol (100 ml) was hydrogenated over 10% palladium on charcoal (250 mg) at 15 p.s.i. (1.04 bar) and room temperature for 18 hours, then filtered. Evaporation of the filtrate under reduced pressure provided the crude product which was purified by column chromatography on silica gel, eluting with dichloromethane:methanol:0.880 aqueous ammonia (90:10:1), to furnish the title compound (291 mg) as a white foam. Rf 0.06 (SS 1). $[\alpha]_D^{25}+50°$ (c=0.1, $CH_3OH$). Found: C,68.77; H,9.19; N,10.22. $C_{23}H_{35}N_3O$; 0.45 $CH_2Cl_2$ requires C,69.07; H,8.87; N,10.30%.

EXAMPLE 3

5-(3-Hydroxy-3-methyl-1-butyl)-3-[N-(N-methane-sulphonyl-3(R,S)-pyrrolidinylmethyl)-2(R)-pyrrolidinylmethyl]-1H-indole Methanesulphonyl chloride (34.1 mg, 23 µl, 0.30 mmol) was added dropwise to a stirred, ice-cooled solution of the title compound of Example 2 (110 mg, 0.27 mmol) and triethylamine (42 µl, 0.30 mmol) in dichloromethane (10 ml) under nitrogen. The reaction mixture was heated under reflux for 24 hours, allowed to cool to room temperature, diluted with dichloromethane (40 ml), washed with 2M aqueous sodium carbonate solution (50 ml), dried ($Na_2SO_4$) and filtered. Evaporation of the filtrate under reduced pressure gave the crude product which was purified by column chromatography on silica gel, eluting with dichloromethane:methanol:0.880 aqueous ammonia (90:10:0.1) to afford the title compound (71 mg) as a white foam. Rf 0.40 (SS 1). $[\alpha]_D^{25}+38°$ (c=0.1, $CH_3OH$). Found: C,62.92; H,8.33; N,8.92. $C_{24}H_{37}N_3O_3S$; 0.17 $CH_2Cl_2$ requires C,62.86; H,8.15; N,9.10%.

EXAMPLE 4

3-[N-(N-Acetyl-3(R,S)-pyrrolidinylmethyl)-2(R)-Pyrrolidinylmethyl]-5-(3-hydroxy-3-methyl-1-butyl)-1H-indole Acetic anhydride (30.6 mg, 28 µl, 0.30 mmol) was added dropwise to a stirred, ice-cooled solution of the title compound of Example 2 (110 mg, 0.27 mmol) in dichloromethane (10 ml) under nitrogen. The reaction mixture was heated under reflux for 4 hours, allowed to cool to room temperature and evaporated under reduced pressure. Residual acetic acid was removed azeotropically using dichloromethane and the crude product purified by column chromatography on silica gel, eluting with dichloromethane:methanol: 0.880 aqueous ammonia (90:10:0.1) to yield the title compound (96 mg) as a white foam. Rf 0.33 (SS 1). $[\alpha]_D^{25}+37°$ (c=0.1, $CH_3OH$). Found: C,69.60; H,8.97; N,9.40. $C_{25}H_{37}N_3O_2$; 0.30 $CH_2Cl_2$ requires C,69.53; H,8.67; N,9.61%.

EXAMPLE 5

5-(3-Hydroxy-3-methyl-1-butyl)-3-[N-(N-methane-sulphonyl-2(R)-pyrrolidinylmethyl)-2(R)-pyrrolidinylmethyl]-1H-indole A stirred mixture of the title compound of Preparation 3 (250 mg, 0.87 mmol), N-methanesulphonyl-2(R)-methanesulphonyloxymethylpyrrolidine (Preparation 5; 247 mg, 0.96 mmol), triethylamine (0.25 ml, 1.75 mmol), 4-dimethylaminopyridine (5.5 mg, 0.04 mmol) and 1,2-dimethoxyethane (5.0 ml), under nitrogen, was heated under reflux for 28 hours and then evaporated under reduced pressure. The residue was dissolved in ethyl acetate (200 ml) and the resulting solution successively washed with 2M aqueous sodium carbonate solution (200 ml) and water (200 ml), dried ($Na_2SO_4$) and evaporated under reduced pressure. The resulting crude product was purified by column chromatography on silica gel, eluting with dichloromethane:methanol (96:4), to furnish the title compound (194 mg) as a foam. Rf 0.41 (SS 1). $[\alpha]_D^{25}+46°$ (c=0.1, $CH_3OH$). Found: C,63.14; H,8.22; N,8.74. $C_{24}H_{37}N_3O_3S$; 0.10 $CH_2Cl_2$; 0.20 $H_2O$ requires C,62.96; H,8.24; N,9.14%

EXAMPLE 6

5-(3-Hydroxy-3-methyl-1-butyl)-3-[N-(N-methanesulphonyl-2(S)-pyrrolidinylmethyl)-2(R)-pyrrolidinylmethyl]-1H-indole The title compound (23% yield) was obtained from the title compound of Preparation 3 by a procedure similar to that described in Example 5, but using N-methanesulphonyl-2(S)-methanesulphonyloxymethylpyrrolidine (Preparation 6) as the alkylating agent, as a foam. Rf 0.42 (SS 1). Found: C,62.61; H,8.12; N,8.82. $C_{24}H_{37}N_3O_3S$; 0.20 $CH_2Cl_2$ requires C,62.56; H,8.11; N,9.04%. LRMS: m/z 448.7 $(M+1)^+$.

EXAMPLE 7

5-(3-Hydroxy-3-methyl-1-butyl)-3-[N-(N-methane-sulphonyl-3(R,S)-pyrrolidinyl)-2(R)-pyrrolidinyl-methyl]-1H-indole The title compound (32% yield) was obtained from the title compound of Preparation 3 by a procedure similar to that described in Example 5, but using N-methanesulphonyl-3(R,S)-methanesulphonyloxypyrrolidine (Preparation 4) as the alkylating agent and dichloromethane:methanol:0.880 aqueous ammonia (95:5:0.1) as the column chromatography eluent, as a foam. Rf 0.40 (SS 1). Found: C,62.99; H,8.12; N,9.36. $C_{23}H_{35}N_3O_3S$; 0.40 $H_2O$ requires C,62.67; H,8.19; N,9.53%. LRMS: m/z 434.0 $(M+1)^+$.

EXAMPLE 8

5-(3-Hydroxy-3-methyl-1-butyl)-3-[N-(2(R)-tetrahydrofuranylmethyl)-2(R)-pyrrolidinylmethyl]-1H-indole and 5-(3-Hydroxy-3-methyl-1-butyl)-3-[N-(2(S)-tetrahydrofuranylmethyl)-2(R)-pyrrolidinylmethyl]-1H-indole The title compounds were obtained from the title compound of Preparation 3 by a procedure similar to that described in Example 1, but using 2(R,S)-tetrahydrofuranylmethyl bromide as the alkylating agent and dichloromethane:methanol: 0.880 aqueous ammonia (90:10:1) as the eluent to effect separation of the diastereoisomers by column chromatography on silica gel, as foams.
Diastereoisomer A (22% yield)
Rf 0.80 (SS 1). $[\alpha]_D^{25}$ -3° (c=0.1, $CH_3OH$). Found: C,67.39; H,8.53; N,6.83. $C_{23}H_{34}N_2O_2$; 0.58 $CH_2Cl_2$ requires C,67.43; H,8.44; N,6.67%.
Diastereoisomer B (30% yield)
Rf 0.72 (SS 1). $[\alpha]_D^{25}$ +14° (c=0.1, $CH_3OH$). Found: C,69.65; H,9.04; N,7.05. $C_{23}H_{34}N_2O_2$; 0.375 $CH_2Cl_2$ requires C,69.77; H,8.70; N,6.96%

The stereochemical identity of each diastereoisomer was not determined and thus it is not known which diastereoisomer corresponds with which title compound.

EXAMPLE 9

5-(3-Hydroxy-3-methyl-1-butyl)-3-[N-(2-oxo-3(R)-piperidylmethyl)-2(R)-pyrrolidinylmethyl]-1H-indole and 5-(3-Hydroxy-3-methyl-1-butyl)-3-[N-(2-oxo-3(S)-piperidylmethyl)-2(R)-pyrrolidinylmethyl]-1H-indole A stirred mixture of the title compound of Preparation 3 (400 mg, 1.40 mmol), 3-methylidene-2-oxo-piperidine (Preparation 10; 172.5 mg, 1.55 mmol) and pyridine (2 ml), under nitrogen, was heated under reflux for 8 days. The cool reaction mixture was diluted with ethyl acetate (250 ml) and washed with 2M aqueous sodium carbonate solution. The combined aqueous washings were extracted with ethyl acetate, then the combined organic solutions dried ($Na_2SO_4$) and evaporated under reduced pressure to yield the crude mixture of diastereoisomers which were separated by column chromatography on silica gel, using an elution gradient of dichloromethane:methanol:0.880 aqueous ammonia (95:5:0.1 to 95:5:0.5), and obtained as foams.
Diastereoisomer A (120 mg)
Rf 0.42 (SS 1). $[\alpha]_D^{25}$ +55° (c=0.1, $CH_3OH$). Found: C,70.23; H,8.83; N,10.02. $C_{24}H_{35}N_3O_2$; 0.20 $CH_2Cl_2$ requires C,70.11; H,8.61; N,10.14%. LRMS: m/z 398.6 $(M+1)^+$.
Diastereoisomer B(52 mg)
Rf 0.31 (SS 1). $[\alpha]_D^{25}$ +11° (c=0.1, $CH_3OH$). Found: C,69.56; H,8.42; N,9.88. $C_{24}H_{35}N_3O_2$; 0.25 $CH_2Cl_2$ requires C,69.55; H,8.54; N,10.03%. LRMS: m/z 398.1 $(M+1)^+$.

The stereochemical identity of each diastereoisomer was not determined and thus it is not known which diastereoisomer corresponds with which title compound.

EXAMPLE 10

5-(3-Hydroxy-3-methyl-1-butyl)-3-[N-(4-tetrahydropyranylmethyl)-2(R)-pyrrolidinylmethyl]-1H-indole The title compound (61% yield) was obtained from the title compound of Preparation 13 by a procedure similar to that described in Example 2 as a foam. Rf 0.48 (SS 1). $[\alpha]_D^{25}$ +34° (c=0.1, $CH_3OH$). Found: C,72.99; H,9.52; N,6.95. $C_{24}H_{36}N_2O_2$; 0.50 $H_2O$ requires C,73.24; H,9.48; N,7.12%.

PREPARATION 1

3-(N-Benzyloxycarbonyl-2(R)-pyrrolidinylmethyl)-5-bromo-1H-indole 3-(N-Benzyloxycarbonyl-2(R)-pyrrolidinylcarbonyl)-5-bromo-1H-indole (WO-A-92/06973; 0.67 g, 1.57 mmol) was dissolved in dry tetrahydrofuran (20 ml) and, at room temperature under nitrogen, lithium borohydride (2M solution in tetrahydrofuran; 1.2 ml, 2.4 mmol) was added. The reaction mixture was stirred at room temperature for 3 hours, heated under reflux for 16 hours, then allowed to cool to room temperature. 2M Hydrochloric acid (10 ml) was added dropwise and the reaction mixture then partitioned between ethyl acetate and water. The separated organic phase was washed with saturated aqueous sodium bicarbonate solution (x2) and brine (x1), dried ($Na_2SO_4$), and evaporated under reduced pressure to give a colourless oil. Purification by column chromatography on silica gel, eluting with dichloromethane, gave the title compound as an oil (0.32 g). Rf 0.20 (SS 16). Found: C,59.94; H,5.07; N,6.58. $C_{21}H_{21}BrN_2O_2$; 0.10 $CH_2Cl_2$ requires C,60.08; H,5.07; N,6.64%.

PREPARATION 2

3-(N-Benzyloxycarbonyl-2(R)-pyrrolidinylmethyl)-5-(3-hydroxy-3-methyl-1-but-1-enyl)-1H-indole A stirred solution of the title compound of Preparation 1 (1.0 mol equiv), 2-methylbut-3-en-2-ol (1.3 mol equiv), tri-o-tolylphosphine (0.3 mol equiv), palladium(II) acetate (0.067 mol equiv) and triethylamine (2.0 mol equiv) in acetonitrile, under nitrogen, was heated under reflux for 24 hours, allowed to cool, then partitioned between ethyl acetate and 2M aqueous sodium carbonate solution. The organic phase was separated, washed sequentially with 2M aqueous sodium carbonate solution (x2) and brine (x1), dried ($Na_2SO_4$) and evaporated under reduced pressure. The crude product was purified by column chromatography on silica gel, eluting with a solvent gradient of dichloromethane:methanol:0.880 aqueous ammonia (95:5:0 to 95:5:0.5), to afford the title compound as a foam. Rf 0.40 (SS 2). $[\alpha]_D^{25}$ -10° (c=0.1, $CH_3OH$). Found: C,73.72; H,6.92; N,6.18. $C_{26}H_{30}N_2O_3$; 0.10 $CH_2Cl_2$ requires C,73.41; H,7.13; N,6.56%.

PREPARATION 3

5-(3-Hydroxy-3-methyl-1-butyl)-3(2(R)-pyrrolidinylmethyl)-1H-indole

A solution of the title compound of Preparation 2 in ethanol was hydrogenated over 10% palladium on charcoal at 15 p.s.i. (1.04 bar) and room temperature for 18 hours, then filtered. Evaporation of the filtrate under reduced pressure yielded an oil, which was azeotroped with dichloromethane (x2) to give a foam. Purification of the foam by column chromatography on silica gel, eluting with a solvent gradient of dichloromethane:methanol:0.880 aqueous ammonia (100:0:0 to 95:5:0 to 96:3.5:0.5), provided the title compound as a foam. Rf 0.10 (SS 1). $[\alpha]_D^{25}$ $-8°$ (c=0.1, $CH_3OH$). Found: C,70.77; H,8.96; N,9.09. $C_{18}H_{26}N_2O$; $H_2O$ requires C,71.02; H,9.27; N,9.20%.

PREPARATION 4

N-Methanesulphonyl-3(R,S)-methanesulphonyloxypyrrolidine

Methanesulphonyl chloride (1.95 ml, 25.3 mmol) was added dropwise to an ice-cooled, stirred solution of 3(R,S)-pyrrolidinol (1.0 g, 11.5 mmol), triethylamine (3.5 ml, 25.3 mmol) and 4-dimethylaminopyridine (70 mg, 0.575 mmol) in dichloromethane (10 ml) under nitrogen. The resulting slurry was stirred at room temperature for 24 hours, then diluted with dichloromethane (50 ml), washed successively with saturated aqueous sodium bicarbonate solution (50 ml) and water 50 ml), dried ($Na_2SO_4$) and filtered. Dilution of the filtrate with ethyl acetate provided the title compound (1.67 g) as a white crystalline solid. Rf 0.84 (SS 1). Found: C,29.89; H,5.12; N,5.74. $C_6H_{13}NO_5S_2$ requires C,29.62; H,5.39; N,5.76%.

PREPARATION 5

N-Methanesulphonyl-2(R)-methanesulphonyloxymethylpyrrolidine

The title compound (66% yield) was obtained from 2(R)-pyrrolidinemethanol by a procedure similar to that described in Preparation 4, but using dilution of an ethyl acetate solution of the product with hexane, followed by chilling, to effect crystallisation. Rf 0.81 (SS 1). Found: C,32.82; H,5.62; N,5.30. $C_7H_{15}NO_5S_2$ requires C,32.67; H,5.88; N,5.44%.

PREPARATION 6

N-Methanesulphonyl-2(S)-methanesulphonyloxymethylpyrrolidine

The title compound (64% yield) was obtained as for Preparation 5, using 2(S)-pyrrolidinemethanol. Rf 0.81 (SS 1). Found: C,32.76; H,5.87; N,5.55. $C_7H_{15}NO_5S_2$ requires C,32.67; H,5.88; N,5.44%.

PREPARATION 7

N-Benzyl-3(R,S)-P-toluenesulphonyloxymethylpyrrolidine

The title compound (69%) was obtained from N-benzyl-3(R,S)-pyrrolidinemethanol (WO-A-91/10650) by a procedure similar to that described in Preparation 4, but using only 1.1 mol. equiv. of p-toluenesulphonyl chloride and triethylamine. The crude product was purified by column chromatography on silica gel, eluting with hexane:ethyl acetate (1:1), to provide a viscous oil. Rf 0.24 (SS 3). Found: C,62.07; H,6.42; N,3.81. $C_{19}H_{23}NO_3S$; 0.33 $CH_2Cl_2$ requires C,62.13; H,6.38; N,3.75%.

PREPARATION 8

Ethyl N-(4-methoxybenzyl)-3-piperidinecarboxylate hydrochloride

A solution of trichloroacetyl chloride (11.1 ml, 99 mmol) in toluene (30 ml) was added dropwise over 45 minutes to a stirred, ice-cooled solution of 4-methoxybenzyl alcohol (12.4 ml, 99 mmol) and N,N-dimethylaniline (12.6 ml, 99 mmol) in toluene (100 ml). The cooling bath was removed and stirring continued at room temperature for 1.5 hours, then the reaction mixture was filtered to remove the N,N-dimethylaniline hydrochloride which was washed with toluene (30 ml). A stirred mixture of the combined filtrate and washings, ethyl 3-piperidinecarboxylate (14.0 ml, 90 mmol) and anhydrous potassium carbonate (13.7 g, 99 mmol), under nitrogen, was heated under reflux for 110 hours, allowed to cool and filtered. Evaporation of the filtrate under reduced pressure gave a brown oil which was dissolved in dichloromethane (100 ml) and the resulting solution washed successively with 2M aqueous sodium carbonate solution (100 ml) and ca. 5M hydrochloric acid (200 ml), dried ($Na_2SO4$) and evaporated under reduced pressure to provide a viscous oil. This oil was stirred at room temperature with a 1:1 mixture of ethyl acetate:hexane (100 ml) to produce a solid which was purified by successive trituration with the same solvent mixture (4×50 ml) to afford the title compound (6.11 g). Rf 0.85 (SS 1). Found: C,59.41; H,7.50; N,4.15. $C_{16}H_{23}NO_3$; HCl; 0.50 $H_2O$ requires C,59.52; H,7.80; N,4.34%

PREPARATION 9

N-(4-Methoxybenzyl)-3-methylidene-2-oxopiperidine

A solution of the title compound of Preparation 8 (4.0 g, 12.75 mmol) and potassium hydroxide (1.43 g, 25.5 mmol) in a 20:1 mixture of methanol:water (126 ml) was stirred for 24 hours and then evaporated under reduced pressure. Residual water was removed azeotropically and then acetic anhydride (120 ml) and triethylamine (18 ml) added to the residue. The resulting mixture was stirred and heated under reflux for 6 hours, then evaporated under reduced pressure. The residue was dissolved in dichloromethane (100 ml) and the solution washed with water (2×100 ml), dried ($MgSO_4$) and evaporated under reduced pressure. The resulting oil was purified by column chromatography on silica gel, eluting with hexane:ethyl acetate (1:1), to furnish the title compound (956 mg). Rf 0.19 (SS 3). Found: C,70.39; H,7.45; N,6.04. $C_{14}H_{17}NO_2$; 0.40 $H_2O$ requires C,70.50; H,7.50; N,5.87%.

PREPARATION 10

3-Methylidene-2-oxopiperidine

A stirred mixture of the title compound of Preparation 9 (917 mg, 3.96 mmol), anisole (726 mg, 7.14 mmol) and trifluoroacetic acid (10 ml) was heated under reflux for 18 hours and allowed to cool. Evaporation under reduced pressure yielded a dark orange oil which was dissolved in ether (25 ml). The solution was extracted with water (3×25 ml) and the combined aqueous extracts saturated with solid potassium carbonate and then extracted with dichloromethane (4×35 ml). Evaporation under reduced pressure of the combined and dried ($Na_2SO_4$) organic extracts provided the title compound (406 mg) as a pale yellow oil. Found: C,64.61; H,8.07; N,12.14. $C_6H_9NO$; 0.01 $CH_2Cl_2$ requires C,64.45; H,8.12; N,12.51%

PREPARATION 11

5-Bromo-3-(2(R)-pyrroldinylmethyl)-1H-indole

The title compound was prepared by any of the following methods.

(A)

A mixture of the title compound of Preparation 1 (10.0 g, 24.2 mmol) and a solution of hydrogen bromide in glacial acetic acid (36% w/w; 17 ml) was stirred at about 0° C. for 1 hour, then the solvent removed under reduced pressure and the residue azeotroped with toluene. The resulting oil was partitioned between dichloromethane and 2M aqueous sodium carbonate solution, then the organic phase separated, combined with a further dichloromethane extract of the aqueous phase, dried ($Na_2SO_4$) and evaporated under reduced pressure. Purification of the crude product by column chromatography on silica gel, eluting with a solvent gradient of dichloromethane:methanol:0.880 aqueous ammonia (95:5:0 to 95:5:2), gave the title compound as an oil (2.01 g). Rf 0.10 (SS 1). $[\alpha]_D^{25}$ $-9°$ (c=0.1, $CH_3OH$). Found: C,54.75; H,5.41; N,9.63. $C_{13}H_{15}BrN_2$; 0.20 $CH_2Cl_2$ requires C,54.84; H,5.37; N,9.67%.

(B)

A solution of the title compound of Preparation 1 (5.0 g, 12.1 mmol) in dichloromethane was added dropwise to a stirred mixture of boron trifluoride etherate (17.15 g, 14.9 ml, 12.1 mmol) and ethanethiol (21.4 g, 25.5 ml, 344 mmol) at room temperature under nitrogen. After 68 hours the reaction mixture was poured into 10% aqueous sodium carbonate solution, then extraction with ethyl acetate (3×400 ml) effected. Evaporation under reduced pressure of the dried ($Na_2SO_4$), combined extracts, followed by column chromatography on silica gel of the crude product, eluting with dichloromethane:methanol:0.880 aqueous ammonia (90:10:1), provided the title compound as a foam (2.10 g). Rf 0.10 (SS 1). $[\alpha]_D^{25}$ $-12°$ (c=0.1, $CH_3OH$). Found: C,55.04; H,5.29; N,9.83. $C_{13}H_{15}BrN_2$; 0.06 $CH_2Cl_2$ requires C,55.10; H,5.35; N,9.83%.

(C)

A saturated solution of hydrogen chloride in methanol (20 ml) was added to a stirred, ice-cooled solution of the title compound of Preparation 1 (10.0 g, 24.2 mmol) in dichloromethane (20 ml) under nitrogen. After 1 hour the ice bath was removed and the reaction mixture stirred at room temperature for 48 hours and then evaporated under reduced pressure. The residual oil was triturated with ether (2×20 ml), then partitioned between ether (50 ml) and water (50 ml). The aqueous phase was washed with ether (2×75 ml), basified with solid sodium carbonate and extracted with ethyl acetate (2×75 ml), then the combined extracts washed with saturated brine, dried ($Na_2SO_4$) and evaporated under reduced pressure. The residue was purified by column chromatography on silica gel, eluting with a solvent gradient of dichloromethane: methanol:0.880 aqueous ammonia (100:0:0 to 90:10:0 to 90:10:1), to afford the title compound as a solid, m.p. 120–123.50° C. Rf 0.15 (SS 1). Found: C,55.06; H,5.33; N,9.59. $C_{13}H_{15}BrN_2$; 0.25 $H_2O$ requires C,55.04; H,5.51; N,9.88%.

(D)

A stirred solution of the title compound of Preparation 1 (360 mg, 0.87 mmol) and potassium hydroxide (1.0 g, 17.8 mmol) in ethanol (20 ml) was heated under reflux for 72 hours. The ethanol was removed by evaporation under reduced pressure and replaced with n-butanol (20 ml), then the resulting mixture stirred under reflux for a further 48 hours and evaporated under reduced pressure. The residue was purified as in (C) above to provide the title compound (73 mg). Rf 0.10 (SS 1).

PREPARATION 12

5-Bromo-3-[N-(4-tetrahydropyranylmethyl-2(R)-pyrrolidinylmethyl]-1H-indole

The title compound (54% yield) was obtained from the title compound of Preparation 11 and 4-p-toluenesulphonyloxymethyltetrahydropyran (J. Amer. Chem. Soc., 1993, 115, 8401) by a procedure similar to that described in Example 1, but using an elution gradient of dichloromethane:methanol:0.880 aqueous ammonia (95:5:0.0 to 95:5:1) for column chromatographic purification, as a sticky solid. Rf 0.83 (SS 1). $[\alpha]_D^{25}$ $+35°$ (c=0.1, $CH_3OH$). Found: C,58.79; H,6.52; N,6.77. $C_{19}H_{25}N_2OBr$; 0.20 $CH_2Cl_2$ requires C,58.45; H,6.49; N,7.10%

PREPARATION 13

5-(3-Hydroxy-3-methyl-1-but-1-enyl)-3-[N-(4-tetrahydropyranylmethyl)-2(R)-pyrrolidinylmethyl]-1H-indole The title compound (40% yield) was obtained from the title compound of Preparation 12 and 2-methylbut-3-en-2-ol by a procedure similar to that described in Preparation 2 but using an elution gradient of dichloromethane:methanol:0.880 aqueous ammonia (92:8:0.25 to 92:8:1) for column chromatographic purification, as a foam. Rf 0.48 (SS 1). $[\alpha]_D^{25}$ $+42°$ (c=0.1, $CH_3OH$). Found: C,74.31; H,8.93; N,6.88. $C_{24}H_{34}N_2O_2$; 0.33 $H_2O$ requires C,74.23; H,8.99; N,7.21%.

Biological activity

The following Table illustrates the in vitro activities for a range of the compounds of the invention on dog isolated saphenous vein strip. $EC_{50}$ represents the concentration of compound which causes 50% of the maximum contraction effected by it.

TABLE

| EXAMPLE | $EC_{50}$ (M) | RELATIVE POTENCY $EC_{50}$ (compound)/ $EC_{50}$ (5-HT) |
|---|---|---|
| 1 | $6.2 \times 10^{-7}$ | 11.0 |
| 5 | $1.8 \times 10^{-7}$ | 2.4 |
| 9A | $3.0 \times 10^{-6}$ | 71 |
| 9B | $1.8 \times 10^{-6}$ | 78 |

Safety profile

One of the compounds of the invention has been tested in conscious dog and showed no overt signs of adverse acute toxicity at doses of up to 0.5 mg/Kg i.v. and 1 mg/Kg p.o.

I claim:

1. A compound of formula (I):

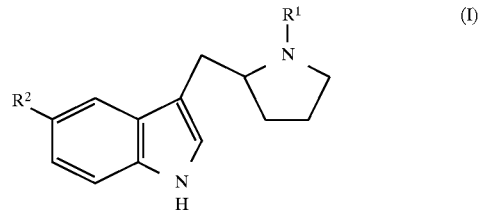

or a pharmaceutically acceptable salt thereof, or a pharmaceutically acceptable solvate of either entity, wherein $R^1$ is

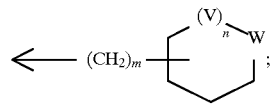

$R^2$ is $R^3R^4C(OH)A$;

V is C=O or $CH_2$;

W is O or NR$^5$;

R$^3$ and R$^4$ are each independently selected from H and C$_1$–C$_4$ alkyl; or, together with the carbon atom to which they are attached, form a 4- or 5-membered carbocyclic ring;

R$^5$ is H, benzyl, C$_1$–C$_5$ alkanoyl or SO$_2$(C$_1$–C$_4$)alkyl;

A is C$_2$–C$_3$ alkylene;

m is 0 or 1;

and n is 0 or 1;

with the provisos that when n is 1 and V is C=O then W is NH, and when n is 1 and V is CH$_2$ then W is O.

2. A compound according to claim 1 wherein W is NR$^5$; R$^3$ and R$^4$ are both methyl; R$^5$ is H, benzyl, COCH$_3$ or SO$_2$CH$_3$; A is ethylene; m is 0 or 1; and n is 0.

3. A compound according to claim 2 wherein R$^5$ is benzyl or SO$_2$CH$_3$; and m is 1.

4. A compound according to claim 1 wherein the preferred stereoisomer has the 2(R)-configuration of formula (IA):

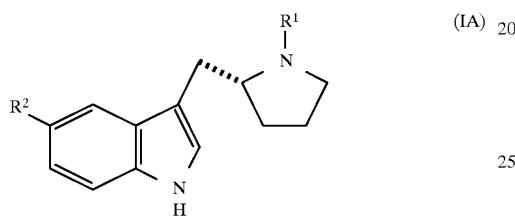

(IA)

wherein R$^1$ and R$^2$ are as previously defined in said claims.

5. A compound according to claim 4 wherein the compound of formula (IA) is selected from 3-[N-(N-benzyl-3(R,S)-pyrrolidinylmethyl)-2(R)-pyrrolidinylmethyl]-5-(3-hydroxy-3-methyl-1-butyl)-1H-indole and 5-(3-hydroxy-3-methyl-1-butyl)-3-[N-(N-methanesulphonyl-2(R)-pyrrolidinylmethyl)-2(R)-pyrrolidinylmethyl]-1H-indole;

or a pharmaceutically acceptable salt thereof, or a pharmaceutically acceptable solvate of either entity.

6. A composition for treating a condition selected from migraine cluster headache, chronic paroxysmal hemicrania, headache associated with a vascular disorder, depression, anxiety, an eating disorder, obesity, drug abuse and emesis comprising an amount of a compound according to claim 1 effective in treating such condition together with a pharmaceutically acceptable diluent or carrier.

7. A method of treating a human being for a condition selected from migraine, cluster headache, chronic paroxysmal hemicrania, headache associated with a vascular disorder, depression, anxiety, an eating disorder, obesity, drug abuse and emesis, which comprises administering to said human being in need of such treatment an amount of a compound according to claim 1 effective in treating such condition.

8. A method of treating a human being for a medical condition for which a selective agonist of 5-HT$_1$-like receptors is indicated, which comprises treating said human being with an amount of a compound according to claim 1 effective in treating such condition.

9. A pharmaceutical composition for treating a human being for a medical condition for which a selective agonist of 5-HT$_1$-like receptors is indicated, comprising an amount of a compound according to claim 1 effective in treating such condition together with a pharmaceutically acceptable diluent or carrier.

* * * * *